United States Patent
Zhang et al.

(10) Patent No.: US 10,960,066 B2
(45) Date of Patent: Mar. 30, 2021

(54) ***STREPTOCOCCUS PNEUMONIAE* VACCINE**

(71) Applicant: Tsinghua University, Beijing (CN)

(72) Inventors: Jing-Ren Zhang, Beijing (CN); Yang Wang, Beijing (CN); Zhensong Wen, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 16/542,497

(22) Filed: Aug. 16, 2019

(65) Prior Publication Data

US 2019/0365880 A1 Dec. 5, 2019

Related U.S. Application Data

(63) Continuation of application No. PCT/CN2017/114577, filed on Dec. 5, 2017.

(30) Foreign Application Priority Data

Feb. 16, 2017 (CN) .......................... 201710084202.2

(51) Int. Cl.
| | | |
|---|---|---|
| *A61K 39/09* | (2006.01) | |
| *A61P 37/04* | (2006.01) | |
| *A61P 31/04* | (2006.01) | |
| *A61P 11/00* | (2006.01) | |
| *C07K 16/12* | (2006.01) | |
| *A61K 39/00* | (2006.01) | |
| *G01N 33/569* | (2006.01) | |

(52) U.S. Cl.
CPC ............ *A61K 39/092* (2013.01); *A61P 11/00* (2018.01); *A61P 31/04* (2018.01); *A61P 37/04* (2018.01); *C07K 16/1275* (2013.01); *G01N 33/56944* (2013.01); *A61K 2039/54* (2013.01); *G01N 2333/3156* (2013.01); *G01N 2800/26* (2013.01)

(58) Field of Classification Search
None
See application file for complete search history.

(56) References Cited

FOREIGN PATENT DOCUMENTS

| | | |
|---|---|---|
| CN | 101066447 | 11/2007 |
| CN | 103501809 | 1/2014 |

OTHER PUBLICATIONS

Xue et al. (FEMS Immunology and Medical Microbiology vol. 58, pp. 202-210).*
Cleary et al. (Vaccine vol. 22, pp. 4332-4341).*
WIPO, ISR for PCT/CN2017/114577, dated Feb. 26, 2018.
SIPO, First Office Action for CN Application No. 201710084202.2, dated Oct. 14, 2019.

* cited by examiner

*Primary Examiner* — Robert A Zeman
(74) *Attorney, Agent, or Firm* — Hodgson Russ LLP

(57) ABSTRACT

Provided is a method of treating or preventing pneumococcal disease. Also provided is a method of diagnosing pneumococcal disease.

10 Claims, 3 Drawing Sheets

STREPTOCOCCUS PNEUMONIAE VACCINE

CROSS-REFERENCE TO RELATED APPLICATIONS

The application is a continuation of PCT Application No. PCT/CN2017/114577, filed on Dec. 5, 2017, which claims a priority to and benefits of Chinese Patent Application No. 201710084202.2, filed China on Feb. 16, 2017, the entire contents of which are incorporated herein by reference.

FIELD

The present disclosure relates to the field of biomedicine. In particular, the present disclosure relates to a method of treating or preventing a Pneumococcal disease and a method of diagnosing pneumococcal disease.

BACKGROUND

S. pneumoniae or pneumococcus is a major bacterial pathogen causing an array of infections such as pneumonia, ear infection (otitis media), meningitis, and septicemia. Several capsular polysaccharide (CPS)-based vaccines of pneumococcus are currently used in the U.S. and certain other countries Europe. However, these vaccines have achieved limited success in the prevention of pneumococcal disease worldwide due to their high costs, poor immunogenicity of capsular polysaccharide in children, and limited coverage of pneumococcal serotypes. There are at least 98 chemically different types of capsular polysaccharides. However, the broadest CSP-based vaccines cover only up to 23 types. In addition, it has been well documented that non-vaccine serotypes are steadily replacing the vaccine serotypes in the U.S. and Europe. Some clinically rare serotypes before vaccination have become the major contributors to pneumococcal disease due to serotype replacement. There is an important need for alternatives for replacement or improvement of the current CPS-based pneumococcal vaccines.

SUMMARY

The present disclosure is intended to solve at least one of the technical problems that exist in the related art to some extent. To this end, the present disclosure provides a method of treating or preventing a SS. pneumoniae-related disease and a method of diagnosing pneumococcal disease. The S. pneumoniae-derived protein used as a pneumococcal vaccine antigen can activate the body's immune system, thus producing an antibody for phagocytosis and killing of S. pneumoniae, thereby effectively treating/preventing pneumococcal disease.

In one aspect, the present disclosure provides in embodiments a method of treating or preventing pneumococcal disease, comprising: administering a therapeutic effective amount of a S. pneumoniae-derived protein to a subject in need thereof, wherein the S. pneumoniae-derived protein is SP148 protein or ScpB protein. The inventors have found that the S. pneumoniae-derived protein can activate the body's immune system, thus serving as an antibody for phagocytosis and killing of S. pneumoniae, thereby effectively treating or preventing pneumococcal disease.

In another aspect, the present disclosure provides in embodiments a method of diagnosing pneumococcal disease, comprising: allowing a biological sample to be in contact with a reagent capable of specifically binding to a S. pneumoniae-derived protein, wherein the S. pneumoniae-derived protein is the SP148 protein or the ScpB protein. The inventors have found that the S. pneumoniae-derived protein selected from the SP148 protein and ScpB protein as antigen can activate the body's immune system. Further, the reagent that is capable of specifically detecting the SP148 protein and/or the ScpB protein can be effectively used in diagnosing the Pneumococcal disease.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the drawings, in which.

DETAILED DESCRIPTION

Figure 1:
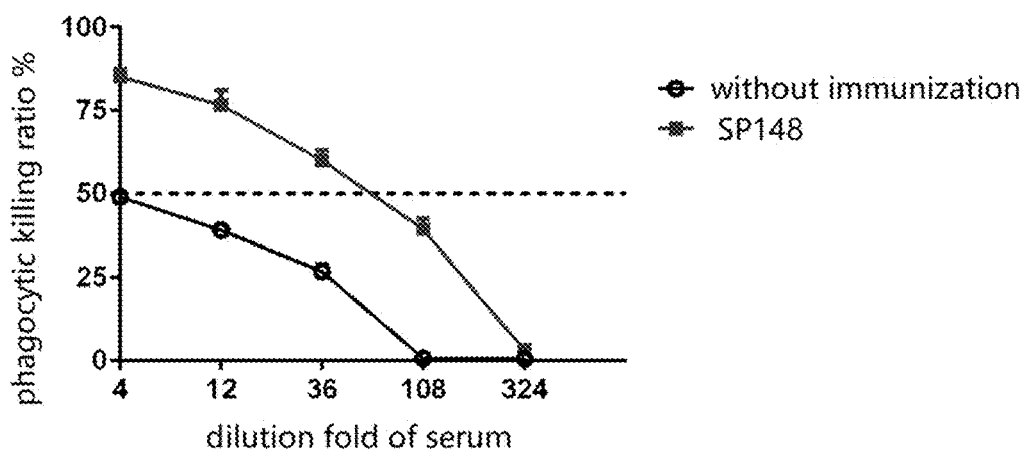
FIG. 1 provides graphs showing the opsonophagocytic killing assay (OPKA) result for the SP148 protein, the Pbp2b protein and the ScpB protein according to one embodiment of the present disclosure.
Figure 1:
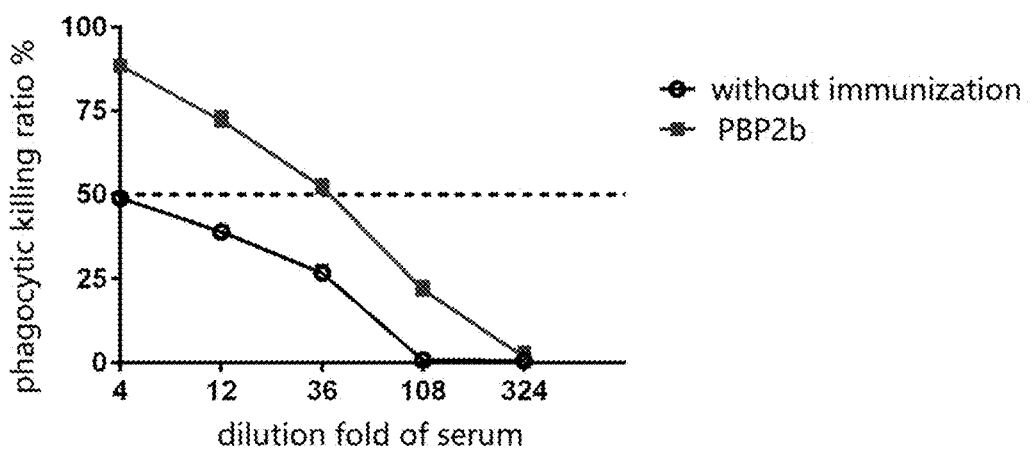
Figure 1:
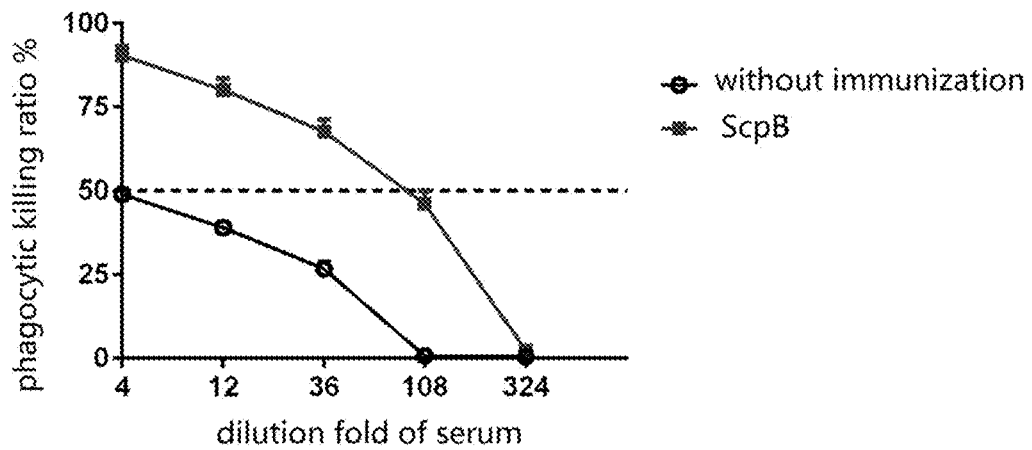

Embodiments of the present disclosure are described in detail below. The embodiments described below are illustrative only and are not to be construed as limiting the disclosure.

The disclosure provides in embodiments a S. pneumoniae vaccine, a method for preparing an antibody, an antibody, an artificial antibody, use of a formulation in the preparation of a medicament, and use of a reagent in the preparation of a kit. This will be described in detail below.

It should be noted that the present disclosure has been completed based on the following findings by the inventors:

Most existing vaccines against S. pneumoniae infection contain a polysaccharide capsule of S. pneumoniae as an antigen for immunization. However, only 23 in around 100 types of polysaccharide capsules with different chemical structures and antigenicity for S. pneumoniae have been developed for the vaccine. At the same time, it has been found in recent years that the S. pneumoniae will develop a new capsular gene through natural transformation, thus generating a new type of polysaccharide capsule which is not targeted by any existing vaccine, resulting in loss of protection by the existing vaccine.

In view of this, the inventors have found that a S. pneumoniae-derived protein selected from the Pbp2b protein, the SP148 protein and the ScpB protein as antigen can elicit an immune response against the S. pneumoniae infection with potent virulence, thus exhibiting immune protection as a vaccine. In addition, bioinformatics analysis showed that the Pbp2b protein, the SP148 protein and the ScpB protein each are of a highly conserved amino acid sequence in *S. pneumoniae* with different types of polysaccharide capsules, thus providing broad-spectrum immune protection.

*S. pneumoniae* Vaccine

In one aspect, the present disclosure provides in embodiments a *S. pneumoniae* vaccine. In some embodiments, the *S. pneumoniae* vaccine includes at least one selected from the followings: (1) at least one *S. pneumoniae*-derived protein selected from the group consisting of the Pbp2b protein, the SP148 protein and the ScpB protein; (2) a nucleic acid encoding (1); (3) a nucleic acid complementary to the nucleic acid as defined in (2); and (4) a nucleic acid having at least 80% homology with at least one of nucleic acids (2) and (3). The inventors have found that the *S. pneumoniae*-derived protein selected from the Pbp2b protein, the SP148 protein and the ScpB protein as antigen can activate the body's immune system, thus producing an antibody for phagocytosis and killing of *S. pneumoniae*, thereby effectively treating/preventing pneumococcal disease. In addition, bioinformatics analysis showed that the Pbp2b protein, the SP148 protein and the ScpB protein each are of a highly conserved amino acid sequence in *S. pneumoniae* with different types of polysaccharide capsules, thus providing broad-spectrum immune protection.

ScpB (putative segregation and condensation protein B) is annotated as segregation and condensation protein in the pneumococcal genome, because it shares 37.3% protein sequence identity with the segregation and condensation protein ScpB of *Bacillus subtilis*. ScpB and ScpA form a complex with the structural maintenance of chromosome protein (SMC), and contribute to chromosome segregation by compacting and organizing the chromosomal DNA.

SP148 is annotated as a periplasmic substrate-binding protein of a putative ATP-binding cassette (ABC) transporter in the pneumococcal genome. SP148 is highly conserved among sequenced *S. pneumoniae* strains.

PBP2b (penicillin-binding protein 2b) is one of the penicillin-binding proteins in *S. pneumoniae*. PBP2b anchors to cell membrane through a hydrophobic sequence at its amino terminus, and functions as a membrane-bound extracellular transpeptidase cross-linking the peptidoglycan layers.

In some embodiments, the vaccine includes at least one *S. pneumoniae*-derived protein selected from the group consisting of the Pbp2b protein, the SP148 protein and the ScpB protein. Thus, the *S. pneumoniae*-derived protein selected from the Pbp2b protein, the SP148 protein and the ScpB protein as antigen can elicit an immune response against the *S. pneumoniae* infection with potent virulence, thus exhibiting immune protection as a vaccine. In addition, bioinformatics analysis showed that the Pbp2b protein, the SP148 protein and the ScpB protein each are of a highly conserved amino acid sequence in *S. pneumoniae* with different types of polysaccharide capsules, thus providing broad-spectrum of immune protection.

In some embodiments, the *S. pneumoniae* vaccine further includes an additional *S. pneumoniae*-derived protein. In a specific embodiment, the additional *S. pneumoniae*-derived protein includes a capsular polysaccharide-conjugated protein. As such, the *S. pneumoniae* vaccine can be used to an enlarged spectrum for *S. pneumoniae* with more different types of polysaccharide capsules, thereby improving therapeutic or prophylactic effect.

Method for Preparing an Antibody

In another aspect, the present disclosure provides in embodiments a method for preparing an antibody against *S. pneumoniae*. In some embodiments, the method includes: (a) immunizing an animal with at least one selected from the followings: (1) at least one *S. pneumoniae*-derived protein selected from the group consisting of the Pbp2b protein, the SP148 protein and the ScpB protein; (2) a nucleic acid encoding (1); (3) a nucleic acid complementary to the nucleic acid as defined in (2); and (4) a nucleic acid having at least 80% homology with at least one of nucleic acids (2) and (3); (b) isolating the antibody from blood of the animal. The inventors have found that the *S. pneumoniae*-derived protein selected from the Pbp2b protein, the SP148 protein and the ScpB protein as antigens can activate the body's immune system, thus producing an antibody for phagocytosis and killing of *S. pneumoniae*, thereby effectively treating and/or preventing pneumococcal disease. Further, the animal's immune system can be activated by immunizing the animal with the Pbp2b protein, the SP148 protein and/or the ScpB protein, the nucleic acids encoding the above proteins and/or complementary nucleic acids thereof, and/or the nucleic acids having at least 80% homology with the above nucleic acids, thereby producing the antibody against *S. pneumoniae*.

In some embodiments, the animal is a mammal selected from a human, a mouse, a dog, a monkey, a sheep, a pig, a rabbit and a camel. Therefore, the antibody against *S. pneumoniae* can be obtained in a high amount.

Antibody

In yet another aspect, the present disclosure provides in embodiments an antibody. In some embodiments, the antibody is prepared by the method for preparing an antibody as described above. The inventors have found that the *S. pneumoniae*-derived protein selected from the Pbp2b protein, the SP148 protein and the ScpB protein can activate the body's immune system, thus obtaining the antibody against *S. pneumoniae*.

Those skilled in the art will appreciate that the features and advantages previously described with respect to the method for preparing antibodies are equally applicable to such an antibody and will not be described herein.

Artificial Antibody

In yet another aspect, the present disclosure provides in embodiments an artificial antibody. In some embodiments, the artificial antibody has an antigenic determinant identical to the antibody described above.

It should be noted that the type of artificial antibody is not strictly limited in the present disclosure, and may be a monoclonal antibody, a polyclonal antibody or a genetically engineered antibody, and the artificial antibody can be obtained in a desired manner according to actual conditions.

Those skilled in the art will appreciate that the features and advantages previously described for the antibody are equally applicable to the artificial antibody and will not be described herein.

Use of a Formulation in the Preparation of a Medicament

In yet another aspect, the present disclosure provides in embodiments use of a formulation in the preparation of a medicament. In some embodiments, the medicament is for treating or preventing a Pneumococcal disease. The formulation includes at least one of the followings: (1) at least one *S. pneumoniae*-derived protein selected from the group consisting of the Pbp2b protein, the SP148 protein and the ScpB protein; (2) a nucleic acid encoding (1); (3) a nucleic acid complementary to the nucleic acid as defined in (2); (4) a nucleic acid having at least 80% homology with at least one of nucleic acids (2) and (3); (5) an antibody as described above and (6) an artificial antibody as described above. The inventors have found that the formulation can activate the body's immune system, thus producing an antibody for phagocytosis and killing of *S. pneumoniae*, thereby effectively treating or preventing pneumococcal disease.

The term "pneumococcal disease" as used herein refers to a disease caused by infections of *S. pneumoniae*, for example, pneumonia, meningitis, otitis media and sepsis.

It should be noted that the term "treatment" or "treating" as used herein refers to achieving a desired pharmacological and/or physiological effect. The effect may be prophylactic in terms of completely or partially preventing a disease or its symptoms, and/or may be therapeutic in terms of partially or completely curing a disease and/or an adverse effect caused by the disease. As used herein, "treatment" or "treating", directing a disease in a mammal, particularly a human, includes: (a) preventing a disease (for example, pneumococcal disease) or a condition from occurring in an individual who is susceptible to the disease but has not yet been diagnosed; (b) inhibiting a disease, for example, retarding progression of the disease; or (c) alleviating a disease, for example, alleviating a disease-related symptom. As used herein, "treatment" or "treating" encompasses any administration of a medicament or compound to an individual to treat, cure, alleviate, improve, ameliorate or inhibit a disease in the individual, including but not limited to, administering a medicament containing the formulation as described herein to an individual in need thereof.

In some embodiments, the administering frequency and dosage of the formulation can be determined by a number of relevant factors including type and severity of a disease to be treated; age, sex, body weight of a subject; administering route; and nature of an active ingredient. In some embodiments, a daily dose may be divided into 1 dose, 2 doses or multiple doses in a suitable form for administration once, twice or more times respectively throughout the time period, as long as a therapeutically effective amount is achieved.

The term "therapeutically effective amount" refers to an amount of a compound that is sufficient to significantly ameliorate a certain symptom associated with a disease or condition, that is, an amount that provides a therapeutic effect for a given condition and dosage regimen. For example, in the treatment of pneumococcal disease, a drug or compound that reduces, prevents, delays, inhibits, or blocks any symptom of a disease or condition should be therapeutically effective. A therapeutically effective amount of a drug or compound does not require a cure for the disease or condition, but will provide a treatment for the disease or condition such that the onset of the disease or condition in the individual is delayed, stopped or prevented, or the symptom of the disease or condition is alleviated, or the duration of the disease or condition is altered, or for example the disease or condition becomes less severe, or the recovery is accelerated. In some specific embodiments, the therapeutically effective amount of the *S. pneumoniae*-derived protein selected from the Pbp2b protein, the SP148 protein or the ScpB protein as a vaccine is 5 μg per dose (corresponding to about 200 μg/kg body weight) for a mouse. Each mouse is immunized three times at an interval of 14 days.

Those skilled in the art will appreciate that the features and advantages previously described for the antibody and artificial antibody are equally applicable to the use of the formulation in the preparation of medicament and will not be described herein.

Use of a Reagent in the Preparation of a Kit

In yet another aspect, the disclosure provides in embodiments the use of an agent in the preparation of a kit. According to an embodiment of the present disclosure, the kit is for diagnosing pneumococcal disease, and the reagent is capable of specifically detecting at least one selected from the followings: (1) at least one *S. pneumoniae*-derived protein selected from the group consisting of the Pbp2b protein, the SP148 protein and the ScpB protein. (2) a nucleic acid encoding (1); (3) a nucleic acid complementary to the nucleic acid as defined in (2); and (4) a nucleic acid having at least 80% homology with at least one of nucleic acids (2) and (3). The inventors have found that the *S. pneumoniae*-derived protein selected from the Pbp2b protein, the SP148 protein and the ScpB protein as antigen can activate the body's immune system. Further, the reagent that is capable of specifically detecting the Pbp2b protein, the SP148 protein and/or the ScpB protein, the nucleic acids encoding the above proteins and/or complementary nucleic acids thereof, and/or the nucleic acids having at least 80% homology with the above nucleic acids can be effectively used in diagnosing pneumococcal disease.

In some embodiments, the reagent includes an antibody or an artificial antibody as described above. Since the antibody and the artificial antibody described above each are capable of specifically binding to any one of the Pbp2b protein, the SP148 protein and the ScpB protein, if the subject is infected with pneumococcal disease, *S. pneumoniae* will by captured by the antibody or the artificial antibody generated by immunization, thus producing a detectable signal for diagnosing pneumococcal disease.

It should be noted that pneumococcal disease is not strictly limited, and may be, for example, pneumonia, meningitis and sepsis caused by infection with *S. pneumoniae*.

Those skilled in the art will appreciate that the features and advantages previously described for the antibody and the artificial antibody are equally applicable to the use of such reagent in the preparation of kits and will not be described herein.

The embodiments of the present disclosure will be explained below in conjunction with examples. Those skilled in the art will appreciate that the following examples are merely illustrative of the disclosure and are not to be considered as limiting the scope of the disclosure. Where specific techniques or conditions are not indicated in the examples, they are carried out according to the techniques or conditions described in the literature in the art or according to the product specifications. The reagents or instruments used that are not indicated about the manufacturer are conventional products that are commercially available.

Example 1 Opsonophagocytic Killing Assay

The Opsonophagocytic Killing Assay refers to the published standard experimental method described as follows. A heat-inactivated serum sample was diluted and mixed with *S. pneumoniae*. After incubation under shaking at room temperature for 30 minutes, differentiated neutrophils and complements were added for additional incubation under shaking at 37° C. for 45 minutes, which was followed by incubation on ice for 10 minutes to terminate reaction. Afterwards, the resulting product was diluted in gradient and then applied onto a medium plate for incubation at 37° C. overnight. A phagocytic killing ratio was determined by counting the number of alive *S. pneumoniae* on the medium plate.

In the Opsonophagocytic Killing Assay, rabbit serum independently immunized with each of the Pbp2b protein, the SP148 protein and the ScpB protein significantly enhances the killing ability of neutrophils against corresponding *S. pneumoniae* compared with non-immunized serum, with 50% phagocytic killing effect achieved over 36-fold dilution (see FIG. 1, the dotted line indicates that the phagocytic killing effect is 50%). This result demonstrates that immunization with each of the Pbp2b protein, the SP148 protein and the ScpB protein can stimulate the production of antibodies in the animal that effectively promote the phagocytosis of S. pneumoniae by the immune system.

Example 2 Immunogenicity Detection of Proteins

5 μg purified SP148 protein and 5 μg purified ScpB protein each were diluted with proper amount of PBS to obtain respective 70 μL mixtures, and the individual mixtures were then added with 30 μL of aluminum hydroxide as an adjuvant to obtain individual experimental injection solutions. The control injection solution consists of 70 μL PBS and 30 μL aluminum hydroxide.

Adult female Balb/c mice were randomly divided into four groups as follow, one was a control group and other three groups were experimental groups.

48 mice in control group were administered by subcutaneous injection with 100 μL control injection solution;

37 mice in Pbp2b protein group were administered by subcutaneous injection with 100 μL experimental injection solution containing 5 μg purified Pbp2b protein;

33 mice in SP148 protein group were administered by subcutaneous injection with 100 μL experimental injection solution containing 5 μg purified SP148 protein; and 32 mice in ScpB protein group were administered by subcutaneous injection with 100 μL experimental injection solution containing 5 μg purified ScpB protein.

All mice were immunized with respective above-indicated proteins three times at an interval of 14 days (i.e., immunized at Day 0, Day 14 and Day 28).

Blood was collected intravenously at Day 35 (i.e the Day 7 from the third immunization) for enzyme-linked immunosorbent assay, with the collected blood serving as a primary antibody and respective purified proteins as the substrate, to determine respective antibody titers. 5 mice in each group were chose for this experiment.

Figure 2:
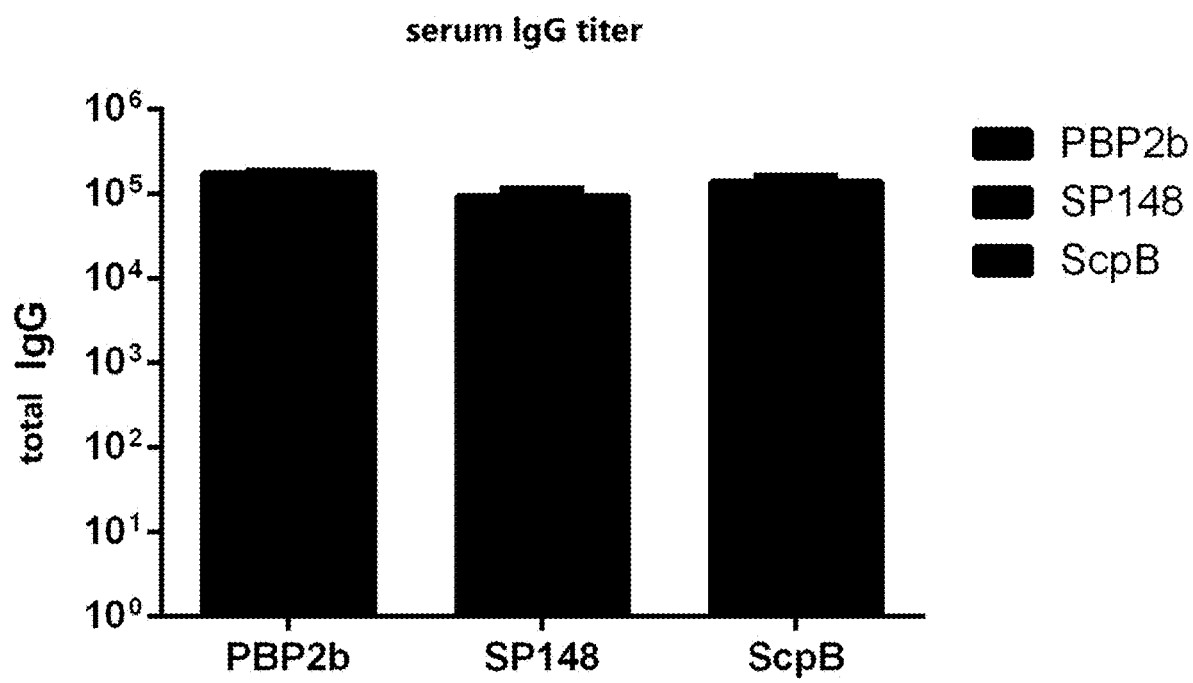
FIG. 2 is a graph showing antibody titer of individual antibodies in serum of immunized mice for the SP148 protein, the Pbp2b protein and the ScpB protein according to one embodiment of the present disclosure.

The results show that after respective subcutaneous injections of Pbp2b protein, SP148 protein and ScpB protein (with aluminum hydroxide as an adjuvant) results in high titer antibodies against the protein antigen in mice (see FIG. 2).

Example 3 Active Immunoprotection Assay—Respiratory Tract Infection 17 mice in the control group, 17 Mice in the Pbp2b protein group, 17 mice in SP148 protein group and 17 mice in ScpB protein group were anesthetized at Day 49 (i.e., Day 21 from the third immunization) and applied with 5×10⁶ S. pneumoniae in suspended in 40 μL PBS through nasal dropping.

After additional 7 days, all selected mice for Respiratory Tract Infection Experiment were sacrificed for tissue and organ collection. In specific, nasal lavage with sterile PBS was conducted to collect a lavage solution, and lung was collected and grinded with sterile PBS to obtain lung homogenate. The lavage solution and lung homogenate were subsequently applied onto respective medium plates for incubation overnight. The number and density of alive S. pneumoniae in were counted and determined for the above four groups.

Figure 3:
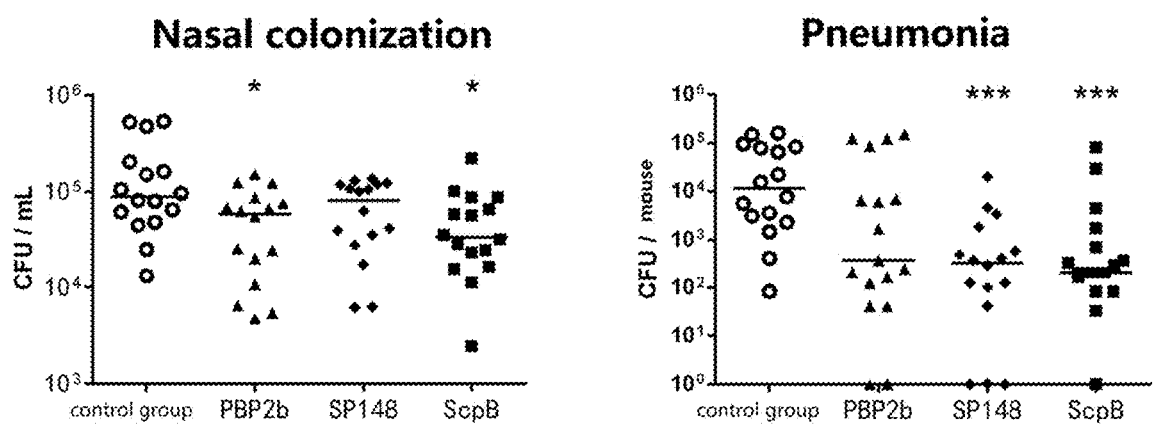
FIG. 3 provides graphs showing respiratory infection assay for the SP148 protein, the Pbp2b protein and the ScpB protein according to one embodiment of the present disclosure.

The results indicate that the Pbp2b protein, the SP148 protein and the ScpB protein each exhibit significant immunoprotective effect. In the respiratory infection model, respective immunizations with the Pbp2b protein and the ScpB protein significantly reduce the density of alive S. pneumoniae in colonized in the nasal cavity of mice, and respective immunizations with the SP148 protein and ScpB protein significantly reduce the number of alive S. pneumoniae in the lung of mice (see FIG. 3).

Example 4 Active Immunoprotection Test—Systemic Infection 26 mice in the control group, 15 mice in the Pbp2b protein group, 11 mice in SP148 protein group and 10 mice in ScpB protein group were intraperitoneally injected with about 100 S. pneumoniae suspended in 100 μL PBS at Day 49 (i.e., Day 21 from the third immunization). Afterwards, all mice in the above-indicated four groups were daily monitored for death and survival during the next 14 days.

Figure 4:
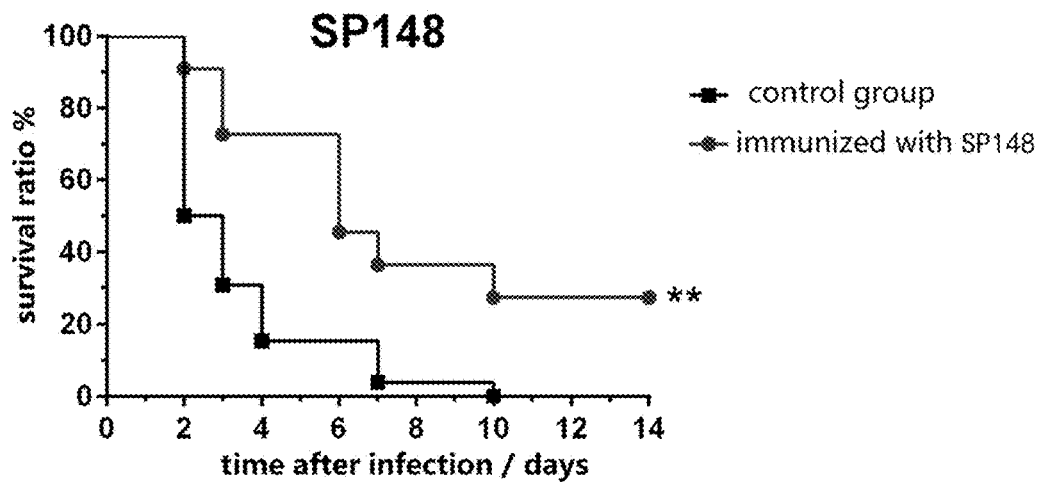
FIG. 4 provides graphs showing a systemic infection assay for the SP148 protein, the Pbp2b protein and the ScpB protein according to one embodiment of the present disclosure.
Figure 4:
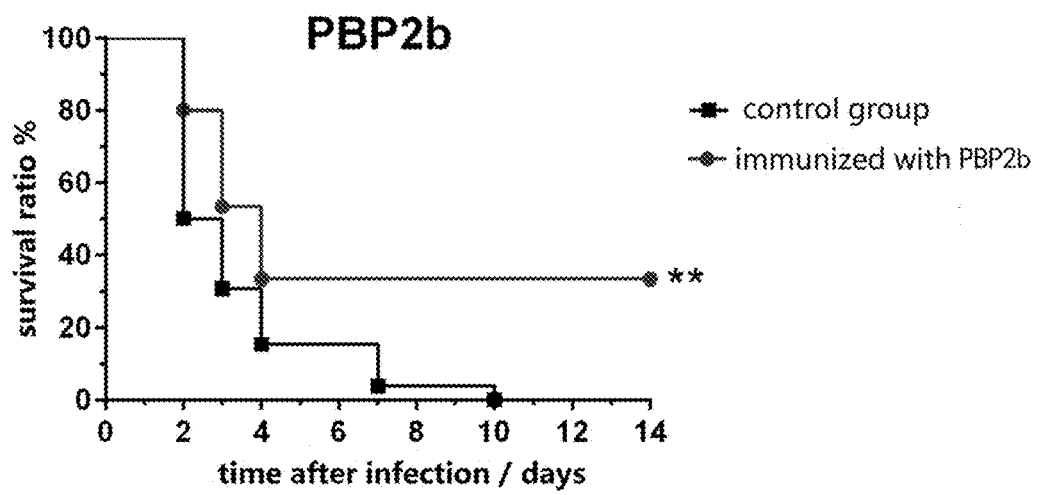
Figure 4:
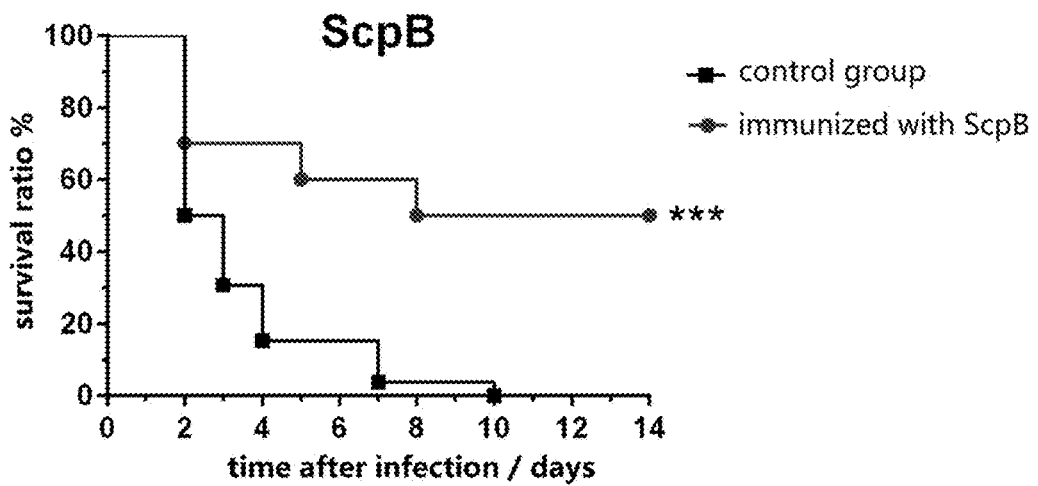

The results show that respective immunization with the Pbp2b protein, the SP148 protein and the ScpB protein can significantly improve the survival rate of mice after injection by intraperitoneal injection of S. pneumoniae (see FIG. 4).

Reference throughout this specification to "one embodiment", "some embodiments", "an example", "a specific example" or "some examples" means that a particular feature, structure, material, or characteristic described in connection with the embodiment or example is included in at least one embodiment or example of the present disclosure. Thus, the appearances of the above phrases in various places throughout this specification are not necessarily referring to the same embodiment or example of the present disclosure. Furthermore, the particular features, structures, materials, or characteristics may be combined in any suitable manner in one or more embodiments or examples. In addition, without contradicting each other, various embodiments or examples described in the specification, as well as features of various embodiments or examples, may be combined.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method of treating a disease caused by *Streptococcus pneumoniae*, comprising: administering a therapeutically effective amount of a *Streptococcus pneumonia* putative segregation and condensation protein B (ScpB) or a formulation comprising the ScpB protein to a subject in need thereof.

2. The method according to claim 1, wherein the disease caused by the *Streptococcus pneumoniae* comprises pneumonia, meningitis, or sepsis.

3. The method according to claim 1, comprising:
    administering the ScpB protein from *Streptococcus pneumoniae* in combination with an a capsular polysaccharide protein.

4. The method according to claim 1, wherein the ScpB protein from *Streptococcus pneumoniae* is administered to the subject subcutaneously.

5. The method according to claim 1. wherein the ScpB protein from *Streptococcus pneumoniae* is administered to the subject at least one time.

6. The method according to claim 5, wherein the ScpB protein from *Streptococcus pneumoniae* is administered to the subject three times.

7. The method according to claim 6, wherein the ScpB protein from *Streptococcus pneumoniae* is administered to the subject three times at an interval of 14 days.

8. The method according to claim 1, wherein the subject is a mammal selected from a human, a mouse, a dog, a monkey, a sheep, a pig, a rabbit, and a camel.

9. The method according to claim 1, wherein the formulation further comprises a pharmaceutically acceptable adjuvant.

10. The method of claim 1, wherein the disease caused by the *Streptococcus pneumoniae* is sepsis.

* * * * *